(12) United States Patent
Eden

(10) Patent No.: US 8,535,937 B2
(45) Date of Patent: *Sep. 17, 2013

(54) DETECTION OF MICROORGANISMS WITH A FLUORESCENCE-BASED DEVICE

(75) Inventor: Gideon Eden, Ann Arbor, MI (US)

(73) Assignee: Neogen Corporation, Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/068,639

(22) Filed: May 17, 2011

(65) Prior Publication Data

US 2011/0248185 A1  Oct. 13, 2011

Related U.S. Application Data

(60) Division of application No. 11/658,341, filed as application No. PCT/US2005/026751 on Jul. 28, 2005, said application No. 11/658,341 is a continuation of application No. PCT/US2005/004331, filed on Feb. 11, 2005.

(60) Provisional application No. 60/592,166, filed on Jul. 29, 2004.

(51) Int. Cl.
*C12M 1/34* (2006.01)

(52) U.S. Cl.
USPC ................................ 435/288.7; 435/287.1

(58) Field of Classification Search
USPC ............. 435/288.7, 30, 32, 34, 261, 287.1, 435/40
See application file for complete search history.

(56) References Cited

U.S. PATENT DOCUMENTS

| | | |
|---|---|---|
| 5,164,301 A | 11/1992 | Thompson |
| 5,173,434 A | 12/1992 | Morris et al. |

(Continued)

FOREIGN PATENT DOCUMENTS

| | | |
|---|---|---|
| CA | 2466433 | 5/2004 |
| DE | 100 38 080.8 | 2/2002 |

(Continued)

OTHER PUBLICATIONS

Gary P. Yakub, David A. Castric, Kathleen L. Stadterman-Knauer, Michael J. Tobin, Mary Blaszina, Tracey N. Heineman, Gim Y. Yee, Lanie Frazier. "Evaluation of Colilert and Enterolert Defined Stubstrate Methodology for Wastewater Applications". Water Environment Research, vol. 74, No. 2, pp. 131-135. Mar./Apr. 2002.*

(Continued)

*Primary Examiner* — Michael Hobbs
(74) *Attorney, Agent, or Firm* — Butzel Long

(57) ABSTRACT

A device and method for detecting by fluorescence microbial growth from sample substances are disclosed. For example, a method for the detection of visible-band fluorescence signals generated by at least one fluorescing compound excited by ultraviolet energy, comprising exciting said at least one fluorescing compound with ultraviolet energy emitted from a light-emitting diode comprising wavelengths below 400 nanometers, and detecting a visible-band fluorescence signal generated by said at least one excited fluorescing compound with at least one light detector sensitive to electromagnetic energy comprising wavelengths greater than or equal to 400 nanometers wavelength. For example, a device for detecting visible-band fluorescence signals generated by at least one fluorescing compound excited by ultraviolet energy, comprising at least one ultraviolet light-emitting diode generating electromagnetic radiation comprising wavelengths below 400 nanometers and capable of exciting the at least one fluorescing compound, at least one light detector sensitive to electromagnetic energy comprising wavelengths greater than or equal to 400 nanometers wavelength for the detection of visible-band fluorescence signals generated by the at least one fluorescing compound.

4 Claims, 1 Drawing Sheet

(56) References Cited

U.S. PATENT DOCUMENTS

| | | | |
|---|---|---|---|
| 5,366,873 A * | 11/1994 | Eden et al. | 435/34 |
| 6,015,715 A | 1/2000 | Kirschner et al. | |
| 6,673,532 B2 | 1/2004 | Rao | |
| 7,041,493 B2 | 5/2006 | Rao | |
| 7,745,169 B2 * | 6/2010 | Eden et al. | 435/40 |
| 2002/0079454 A1 | 6/2002 | Yamada | |
| 2004/0121453 A1 * | 6/2004 | Rao | 435/287.3 |
| 2005/0254055 A1 * | 11/2005 | Peng | 356/432 |
| 2005/0266516 A1 * | 12/2005 | Kanipayor et al. | 435/34 |

FOREIGN PATENT DOCUMENTS

| | | |
|---|---|---|
| JP | 61140843 A | 7/1986 |
| JP | 7146236 A | 6/1995 |
| JP | 8043308 A | 2/1996 |
| JP | 2002159447 A | 6/2002 |
| JP | 2002350732 A | 12/2002 |
| JP | 2002355024 A | 12/2002 |
| JP | 2003102671 A | 4/2003 |
| JP | 2003190103 A | 7/2003 |
| JP | 2003270137 A | 9/2003 |
| WO | WO0128006 | 4/2001 |

OTHER PUBLICATIONS

Ulrich Schreiber, Leslie Groberman, and William Vidaver. Portable, solid-state fluorometer for the measurement of chlorophyll fluorescence induction in plants, Rev.Sci.Instrum., vol. 46, No. 5, May 1975, p. 538 to 542.

Correspondence to Ian C. McLeod from Denise M. Glassmeyer (Young Basile Hanlon & MacFarlane, P.C.) dated Dec. 11, 2009.

* cited by examiner

DETECTION OF MICROORGANISMS WITH A FLUORESCENCE-BASED DEVICE

This application is a Division of U.S. application Ser. No. 11/658,341, filed on Oct. 14, 2008, which is a 371 of PCT/US05/26751, filed on Jul. 28, 2005, which claims the benefit of U.S. Provisional Application Ser. No. 60/592,166, filed Jul. 29, 2004, and which is a Continuation of PCT/US05/04331, filed on Feb. 11, 2005, which claims the benefit of U.S. Provisional Application Ser. No. 60/592,166, filed Jul. 29, 2004, which are incorporated herein by reference.

BACKGROUND OF THE INVENTION

The present invention relates to fluorescence-based devices for detecting microbial growth from test samples.

It is necessary to test various industrial substances, such as food, pharmaceuticals, cosmetics and water, for microbial contamination. One area of biological testing of food, dairy, pharmaceutical, cosmetic and related types of products involves the estimation of total numbers of bacteria, yeasts and molds, as well as concentrations of specific groups of organisms within the material. One widely used method is known as the "Standard Plate Count" method and involves culturing a diluted sample of the product in an agar growth medium. The plates containing the sample and the growth medium are incubated (e.g., 32° C.-40° C.) for 24 hours to 5 days, depending upon the assay. After incubation, colonies of microorganisms which have grown in the agar are counted:

Optical methods have been successfully used to classify microorganisms in clinical samples (e.g., PASCO by Difco, Detroit, Mich.). Although it would be desirable to utilize a colorimetric method, or any other optical method, for detecting microbial growth in industrial samples, the solid substances of the test samples disposed in an aqueous media usually cause optical interference for a detection system. More specifically, when solid substances are disposed in a media to allow for culturing microorganisms, the colorimetric detection system must pass light either through or reflect light from the media containing the solid substance. In most of the cases, the solid substances interfere with the spectral characteristics of the media, yielding a poor signal-to-noise ratio of the detection system.

A device for continuously monitoring the biological activity in a specimen is described by Eden in U.S. Pat. No. 5,366,873. It describes a device and method for detecting microbial growth from a sample substance. The device includes a container which is at least partially transparent and fluid disposed in the container for cultivating microorganisms therein. An indicator substance is disposed in the fluid layer for undergoing transformation in the presence of microorganism growth. A second layer, composed of semi fluid substance, indicators and other substances, such as growth media, is disposed in the container. The substances within the semi-fluid phase are in equilibrium with the substances in the fluid layer and provide a barrier to solid substances introduced into the fluid layer while providing a zone within which changes in the indicator substance, due to microbial growth, can be detected. In practice, the indicator substance has been dyes that are affected by the PH variations in the fluid layer.

SUMMARY OF THE INVENTION

The present invention extends the scope of the above patent by employing fluorescing indicator substances to enhance the measurement sensitivity and the group of detected microorganisms. In certain embodiments of the present invention, there is provided a device and method for detecting microbial growth from a sample substance. The device can comprise at least one container which is at least partially transparent to electromagnetic radiation in the visual and/or the ultraviolet wavelength ranges and fluid disposed in the at least one container for cultivating microorganisms therein. At least one fluorescing indicator substance can be disposed in the fluid layer for undergoing transformation in the presence of microorganism growth. A second layer, composed of at least one semi-fluid substance, indicators and other substances, such as growth media, can be disposed in the container. The substances within the semi-fluid phase can be in equilibrium with the substances in the fluid layer and can provide a barrier to solid substances introduced into the fluid layer while providing a zone within which fluorescence changes in the indicator substance due to microbial growth can be detected.

One embodiment of the invention relates to a method for the detection of visible-band fluorescence signals generated by at least one fluorescing compound excited by ultraviolet energy, comprising:

exciting the at least one fluorescing compound with ultraviolet energy emitted from a light-emitting diode comprising wavelengths below 400 nanometers; and detecting a visible-band fluorescence signal generated by the at least one excited fluorescing compound with at least one light detector sensitive to electromagnetic energy comprising wavelengths greater than or equal to 400 nanometers.

Another embodiment of the invention relates to method for the detection of visible-band fluorescence signals generated by at least one fluorescing compound excited by ultraviolet energy, comprising:

exciting the at least one fluorescing compound with ultraviolet energy; and detecting a visible-band fluorescence signal generated by the at least one excited fluorescing compound with a light detector sensitive to electromagnetic energy comprising wavelengths greater than or equal to 400 nanometers.

Yet another embodiment of the present invention relates to a device for detecting visible-band fluorescence signals generated by at least one fluorescing compound excited by ultraviolet energy, comprising:

at least one ultraviolet light-emitting diode generating electromagnetic radiation comprising wavelengths below 400 nanometers and capable of exciting the at least one fluorescing compound; and at least one light detector sensitive to electromagnetic energy comprising wavelengths greater than or equal to 400 nanometers for the detection of visible-band fluorescence signals generated by the at least one fluorescing compound.

A further embodiment of the present invention relates to a device for detecting visible-band fluorescence signals and visible-band secondary signals generated by at least one fluorescing compound excited by ultraviolet and visible-band energy, comprising:

at least one ultraviolet ligh+t-emitting diode generating electromagnetic radiation comprising wavelengths below 400 nanometers, the ultraviolet light-emitting diode capable of exciting the at least one fluorescing compound, thereby generating the visible-band fluorescence signal;

at least one visible-band light-emitting diode generating electromagnetic radiation comprising wavelengths greater than or equal to 400 nanometers, the visible-band light-emitting diode capable of interacting with at least one visible dye compound, thereby generating the visible-band secondary signal; and at least one light detector sensitive to electromagnetic energy comprising wavelengths greater than or equal to 400 nanometers for detecting the visible-band fluorescence signal and the visible-band secondary signal.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Generally, the present invention provides a device for detecting microbial growth from a sample substance wherein the device includes at least one container which is at least partially transparent to visual and/or ultraviolet (UV) radiation. A fluid layer can be disposed in the container for cultivating microorganisms therein. A fluorescing indicator substance can be disposed in the fluid layer for undergoing transformation in the presence of microorganism growth. A barrier layer can be disposed in the container which is a semi-fluid substance, the fluid portion of which is the same composition as the fluid layer in which the microorganisms are cultivated. Therefore, the fluid in the semi-fluid layer is in equilibrium with the fluid layer. The semi-fluid substance provides a barrier to solid substances introduced into the fluid layer while providing a zone within which changes in the at least one fluorescing indicator substance, due to microbial growth, can be detected.

More specifically, the barrier layer can be comprised of gelling agents, such as agar. In carrying out the present invention, any type of gelling substance or agar, as defined in the Merck Index, can be utilized. There are several commercial gelling products available which are suitable, including gelatin, carrageenan and pectin.

The important property of such gelling agents used in the present invention is their ability to transfer ions, such as H+ and small molecules, while blocking out bacteria and larger debris particles. If the concentration of the small particles changes due to organism growth (e.g., pH or Redox reactions), the concentration of the identical particles in the barrier layer will track those changes as well. The diffusion coefficient of the barrier layer determines the rate in which variations in the liquid layer are tracked by identical changes in the barrier layer.

Figure 1:
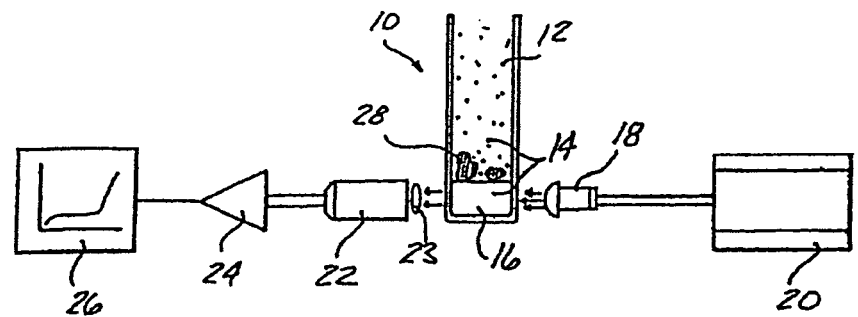
FIG. 1 shows one embodiment of the present invention.

FIG. 1 illustrates a typical configuration of the various components of a system which can be utilized in accordance with this invention. The vial 10 is made of UV-transparent material (e.g., glass, UV-transparent plastics). The barrier layer 16 may be composed of any available agar (e.g., Muller Hinton Agar by Difco, Detroit, Mich.) and non-toxic fluorescing dye 14, such as Umbelliferon. This layer can be manufactured by dispensing the mixture, thermally sterilized, to the bottom of the vial 10 and letting it solidify at room temperature. A sterile mixture of the liquid media 12 and dye 14 is poured at room temperature on top of the barrier layer.

The test sample 28 is placed in the fluid layer. The vial 10 is then placed in an incubating device, at an appropriate temperature, to promote growth of organisms. The incubating device can be an air incubator, heating and cooling blocks or heat exchanger.

An ultraviolet light source 18 is positioned at the bottom part of the vial 10 such that the transmitted UV light is directed through the UV-transparent walls of the vial 10 and the barrier layer 16. The light source can comprise any long or short wave ultraviolet from various UV sources. For example, greater than 50% of the wavelengths from the light source can be below 400 nanometers. In certain embodiments, at least 75% of the wavelengths from the light source can be below 400 nanometers, for example, at least 85% of the wavelengths from the light source can be below 400 nanometers, and at least 95% of the wavelengths from the light source can be below 400 nanometers.

Light emitting diodes (LED) can be used to provide the ultraviolet light. In embodiments of the present invention, greater than 50% of the light generated by the light emitting diode can have a wavelength below 400 nanometers, such as, for example, greater than 75%, greater than 85%, and greater than 95%. In an embodiment of the invention, a long wavelength ultraviolet Light Emitting Diode (e.g., 350 to 400 nanometers) can be utilized.

In another embodiment of the present invention, a multiplicity of light emitting diodes can be controlled by the controller 20, which provides electrical energy which can be spatially uniform and stable.

Figure 2:
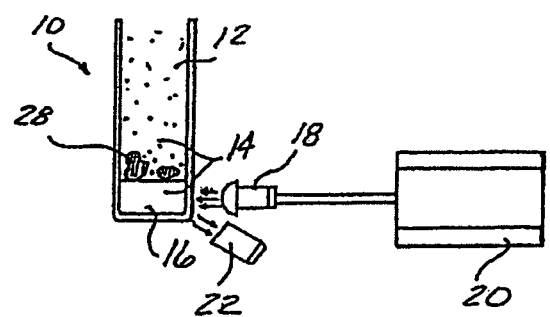
FIG. 2 shows another embodiment of the present invention.

Suitable materials that can be used as the at least one fluorescing compound include materials that emit visible light upon exposure to ultraviolet radiation, such as, for example, umbelliferons and coumarins. In dealing with fluorescing essays, one should remember that the wavelength of the radiation emitted from the fluorescing compound is longer than that of the light source. For example, radiating umbelliferon with a UV light source of 380 nanometers (invisible) generates a blue-green visible radiation. Consequently, care should be taken that the light sensor will not be influenced by stray light generated by the UV light source. If the UV source 18 is placed directly facing the light sensor 22, as shown in FIG. 1, an additional band pass optical filter 23 is required to block the influence of the UV radiation on the sensor. Alternatively, the UV light source 18 and the sensor 22 can be placed next to each other facing the UV-transparent section of the vial at specific angles, as shown in FIG. 2, so that the fluorescing radiation is reflected back to the light sensor. Since the fluorescing radiation is equally radiated in all directions, the specific angles can be set to minimize UV reflected light, thereby allowing the light sensor to measure only the fluorescing energy.

The dynamic changes of the fluorescing light, which is the indicator of bacterial activity, is converted to electrical energy utilizing a light sensor 22. Although a wide variety of sensors may be utilized (e.g., photo voltaics, photodiodes, phototransistors, photo multipliers, charged coupled devices (CCD) and multi-channel devices) low-cost solid state sensors can be employed due to the high energy of light reaching the sensor. Therefore, each vial can have its own pair of light source and sensor, thus eliminating complex mechanical indexing devices utilized in optical readers and thereby increasing the reliability and the operating life of the instrument. The light emitting diode can provide either stationary (constant) or pulsated energy. If an additional light emitting diode operating in the visible range is employed, one of the light emitting diodes can be driven at a constant level of energy while the other can be pulsated, allowing a single light sensor to detect both signals. In another embodiment, both UV light emitting diode and the visible-range light emitting diode can be combined in a single package forming dual-band UV and visible light sources that can be independently activated.

In one embodiment of the invention, readings are taken every six minutes, and the analog data can be converted by the converter 24 to digital form. The process data can be transferred to a processor 26, where it can be displayed, stored and analyzed for real time detection.

The gelling agent or agar can be positioned in the container such that it can be in a transparent region of the container to facilitate measurement of changes in this phase of the system when in use. If the container is a vial or tube, typically the agar could be placed at the bottom of such receptacle, as illustrated in FIG. 1, and would be approximately 2 to 3 mm thick. The agar also could be in the form of a disc, attached to any wall of the container or other configuration as may be convenient in accomplishing the measurement which is an object of the present invention.

The semi-fluid layer (e.g., the agar or gelling phase) can be situated in the liquid phase within the container such that the liquid substances within the agar are in equilibrium with the remaining liquid in the container. In the practice of the present invention, the liquid phase within the container can be a liquid medium suitable for culturing microorganism growth. A sample of a substance which may harbor microorganisms can be placed in the liquid phase in the container and incubated to promote growth of the microorganisms. When microorganisms are present, their growth will result in changes in the composition of the liquid phase throughout the container inasmuch as the liquid in the semi-fluid or agar phase can be in equilibrium with the remainder of the liquid in the container. The contents of the liquid growth medium can be selected to result in a wide variety of changes in the liquid composition that can, be detected and measured, as set forth in more detail below. The change in the composition of the liquid growth medium can be detected and measured in the semi-fluid phase, which can be free of the sample that can be being tested and free of microorganisms. The sample being tested is usually too large molecularly to penetrate the agar phase, as are the microorganisms. Thus, the semi-fluid phase provides a zone within which changes in the liquid phase, brought on by microorganism growth, can be readily detected and measured without any interference from the test sample.

The liquid phase of the present invention can be a medium suitable for the promotion of microorganism growth and for the maintenance of the viability of the microorganisms. Such growth media are well known in the art.

After a test sample has been placed in the liquid phase of the container, the container can be incubated at an appropriate temperature (e.g., about 15° C. to 65° C.) for about 24 to 48 hours, or some other suitable time period, after which changes in the at least one fluorescing substance can be measured. Changes in the at least one fluorescing substance are detected and measured in the semi-fluid phase by analyzing the fluorescence changes related to microorganism growth. Changes in the indicator substance can be detected and measured in the semi-fluid phase since the liquid in this phase can be in equilibrium with the remaining liquid in the container. Thus, any changes which occur in the fluorescence substance will be present throughout the container. Detection and measurement in the semi-fluid phase free of large molecules (e.g., the sample being tested) and microorganisms provides an accurate and consistent means of detecting microorganism growth with a high signal-to-noise ratio.

The container used in the present invention can be glass or long UV-transparent plastics, such as polystyrenes. The entire container need not be transparent, but the portion of the container surrounding the semi-fluid phase must be transparent to permit measurement of any change in the indicator substance in response to microorganism growth. Also, the container can be any shape or size, but typically will be a vial or a tube which can be closed once the agar phase and liquid phase are incorporated therein. Once the two phases are loaded in the container, they can be shipped to the site needed for performing analysis of test samples. No special temperature or storage requirements for the container exist.

In an embodiment of the present invention, a multiplicity of fluorescing compounds can be excited by a multiplicity of light emitting diodes in order to cause the fluorescing compounds to emit visible light. The fluorescing compounds can be present in the same container prior to excitement with the light emitting diodes, or the fluorescing compounds can be present in different containers prior to excitement. In certain embodiments, a single light detector or a multiplicity of light detectors can be used. In certain embodiments, a multiplicity of containers are used, with each container having its own light emitting diode and its own light detector.

In certain embodiments of the invention comprising at least one ultraviolet light emitting diode and at least one visible-band light emitting diode, one of the light emitting diodes can be generating stationary energy and the other light emitting diode can be pulsated, thereby generating a combination of constant energy and pulsated energy directed to the light detector and corresponding to the individual fluorescence signal and the secondary signal. The ultraviolet light emitting diode and visible-band light emitting diode can be packaged in a single enclosure, thereby forming a dual band light emitting diode.

In one embodiment of the invention comprising at least one ultraviolet light emitting diode and at least one visible-band light emitting diode, one of the light emitting diodes can be activated for a specific amount of time while the other light emitting diode can be deactivated, followed by activating the deactivated light emitting diode and deactivating the activated light emitting diode; thereby alternately generating the fluorescence signal and the secondary signal at consecutive periods of time.

In a further embodiment of the invention comprising at least one ultraviolet light emitting diode and at least one visible-band light emitting diode, the interaction of the visible-band light emitting diode with the at least one visible dye compound defines the optical transmittance of the at least one visible dye compound.

Suitable visible dyes compounds include, for example, pH indicators such as Bromcresol Purple, Phenol Red, Bromcresol Green, Bromphenol Blue, Bromthymol Blue; and Redox indicators such as resazurin, methylene Blue, tetrazolium and thionine.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The invention claimed is:
1. A device for detecting microbial growth, comprising:
 (a) a vial containing a fluid for cultivating a microorganism, the vial including a barrier to solid substances in the fluid for separating a zone in which the microorganism is cultivated from a detection zone, the fluid containing at least one indicator substance that emits a visible fluo- rescence signal when excited by ultraviolet energy and at least one visible dye compound capable of generating a visible secondary signal upon interaction with visible light wherein dynamic changes of the emitted signals are indicative of microbial growth;

(b) at least one ultraviolet light-emitting diode positioned adjacent to a first transparent wall of the vial below the barrier generating electromagnetic radiation comprising wavelengths below 400 nanometers into the detection zone, said at least one ultraviolet light-emitting diode capable of exciting said at least one indicator substance, thereby generating said visible fluorescence signal;

(c) at least one visible-band light-emitting diode positioned adjacent to a second transparent wall of the vial below the barrier generating electromagnetic radiation comprising wavelengths greater than or equal to 400 nanometers into the detection zone, said at least one visible-band light-emitting diode capable of interacting with the at least one visible dye compound, thereby generating said visible-band secondary signal;

(d) at least one light detector adjacent to a third transparent wall of the vial sensitive to electromagnetic energy comprising wavelengths greater than or equal to 400 nanometers for detecting said visible-band fluorescence signal and said visible-band secondary signal; and (e) a controller programmed to selectively energize the ultraviolet light-emitting diode and the visible band light-emitting diode wherein the controller energizes one of said light emitting diodes continuously and provides another light-emitting diode with pulsated energy.

2. The device of claim 1, wherein said at least one ultraviolet light-emitting diode and said at least one visible-band light emitting diode are packaged in a single enclosure.

3. The device of claim 1, wherein the interaction of said visible-band light-emitting diode with said at least one visible dye compound defines the optical transmittance of said at least one visible dye compound.

4. A device for detecting microbial growth, comprising:

(a) a vial containing a fluid for cultivating a microorganism, the vial including a barrier to solid substances in the fluid for separating a zone in which the microorganism is cultivated from a detection zone, the fluid containing at least one indicator substance that emits a visible fluorescence signal when excited by ultraviolet energy and at least one visible dye compound capable of generating a visible secondary signal upon interaction with visible light wherein dynamic changes of the emitted signals are indicative of microbial growth;

(b) at least one ultraviolet light-emitting diode positioned adjacent to a first transparent wall of the vial below the barrier generating electromagnetic radiation comprising wavelengths below 400 nanometers into the detection zone, said at least one ultraviolet light-emitting diode capable of exciting said at least one indicator substance, thereby generating said visible fluorescence signal;

(c) at least one visible-band light-emitting diode positioned adjacent to a second transparent wall of the vial below the barrier generating electromagnetic radiation comprising wavelengths greater than or equal to 400 nanometers into the detection zone, said at least one visible-band light-emitting diode capable of interacting with the at least one visible dye compound, thereby generating said visible-band secondary signal;

(d) at least one light detector adjacent to a third transparent wall of the vial sensitive to electromagnetic energy comprising wavelengths greater than or equal to 400 nanometers for detecting said visible-band fluorescence signal and said visible-band secondary signal; and (e) a controller programmed to selectively energize the ultraviolet light-emitting diode and the visible band light-emitting diode, wherein the controller alternately energizes one light-emitting diode while another light-emitting diode is de-energized.

* * * * *